(12) United States Patent
Srivastava et al.

(10) Patent No.: US 12,090,142 B2
(45) Date of Patent: Sep. 17, 2024

(54) COMBINATION THERAPY FOR THE TREATMENT OF CANCER

(71) Applicant: The Board of Regents of the University of Texas System, Austin, TX (US)

(72) Inventors: Satish K. Srivastava, Galveston, TX (US); Kota V. Ramana, Galveston, TX (US); Ashish Saxena, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 246 days.

(21) Appl. No.: 16/975,092

(22) PCT Filed: Feb. 22, 2019

(86) PCT No.: PCT/US2019/019134
§ 371 (c)(1),
(2) Date: Aug. 21, 2020

(87) PCT Pub. No.: WO2019/165195
PCT Pub. Date: Aug. 29, 2019

(65) Prior Publication Data
US 2021/0085650 A1    Mar. 25, 2021

Related U.S. Application Data

(60) Provisional application No. 62/633,820, filed on Feb. 22, 2018.

(51) Int. Cl.
*A61P 35/00*    (2006.01)
*A61K 31/4188*    (2006.01)
(Continued)

(52) U.S. Cl.
CPC ...... *A61K 31/4188* (2013.01); *A61K 39/3955* (2013.01); *A61P 35/00* (2018.01); *C07K 16/2818* (2013.01); *A61K 2039/505* (2013.01)

(58) Field of Classification Search
CPC ............ A61K 31/4188; A61K 39/3955; A61K 2039/505; A61K 39/39558; A61K 45/06; A61P 35/00; C07K 16/2818
See application file for complete search history.

(56) References Cited

U.S. PATENT DOCUMENTS 4,130,714 A    12/1978 Sarges
4,251,528 A    2/1981 Brittain et al.
(Continued)

FOREIGN PATENT DOCUMENTS

EP           2320940       5/2011
WO      WO 96/40173    12/1996
(Continued)

OTHER PUBLICATIONS

Larsson et al. Diabetes Mellitus and Risk of Colorectal Cancer: A Meta-Analysis. Journal of the National Cancer Institute (2005) 97(22): 1679-1687 (Year: 2005).*
(Continued)

*Primary Examiner* — Joanne Hama
*Assistant Examiner* — Gabrielle A Small

(57) ABSTRACT

Certain embodiments are directed to methods and compositions for treating cancer, specifically colorectal cancer by administering an aldose reductase inhibitor and an immune checkpoint inhibitor to a subject in need thereof. Certain embodiments are directed to methods of treating a subject having cancer comprising, administering (i) a composition comprising an aldose reductase specific inhibitor and (ii) a
(Continued)

A

B composition comprising an immune checkpoint inhibitor to the subject having melanoma, head and neck, or colorectal cancer.

7 Claims, 7 Drawing Sheets

(51) Int. Cl.
*A61K 39/00* (2006.01)
*A61K 39/395* (2006.01)
*C07K 16/28* (2006.01)

(56) References Cited

U.S. PATENT DOCUMENTS

| | | | |
|---|---|---|---|
| 4,436,745 | A | 3/1984 | York, Jr. |
| 4,438,272 | A | 3/1984 | York, Jr. |
| 4,464,382 | A | 8/1984 | Tanouchi et al. |
| 4,540,704 | A | 9/1985 | Ueda et al. |
| 4,600,724 | A | 7/1986 | Sestanj et al. |
| 4,734,419 | A | 3/1988 | Hashimoto et al. |
| 4,771,050 | A | 9/1988 | Meguro et al. |
| 4,791,126 | A | 12/1988 | Tanouchi et al. |
| 4,831,045 | A | 5/1989 | Tanouchi et al. |
| 4,883,800 | A | 11/1989 | Hashimoto et al. |
| 4,980,357 | A | 12/1990 | Goldstein et al. |
| 5,037,831 | A | 8/1991 | Malamas |
| 5,066,659 | A | 11/1991 | Lipinski |
| 5,252,572 | A | 10/1993 | Hermecz et al. |
| 5,270,342 | A | 12/1993 | Brittain et al. |
| 5,334,711 | A | 8/1994 | Sproat et al. |
| 5,430,060 | A | 7/1995 | Brittain et al. |
| 5,447,946 | A | 9/1995 | Kurono et al. |
| 5,484,596 | A | 1/1996 | Hanna, Jr. et al. |
| 5,550,214 | A | 8/1996 | Eberlein et al. |
| 6,333,028 | B1 | 12/2001 | Berd |
| 8,008,449 | B2 | 8/2011 | Korman et al. |
| 8,217,149 | B2 | 7/2012 | Irving et al. |
| 2012/0177645 | A1 | 7/2012 | Langermann et al. |
| 2012/0238609 | A1 | 9/2012 | Srivastava et al. |
| 2012/0294796 | A1 | 11/2012 | Johnson et al. |
| 2014/0206693 | A1* | 7/2014 | Srivastava .......... A61K 31/4747 514/266.3 |
| 2017/0334995 | A1* | 11/2017 | Zettl ...................... A61P 43/00 |

FOREIGN PATENT DOCUMENTS

| | | |
|---|---|---|
| WO | WO 00/09140 | 2/2000 |
| WO | WO 2008/002678 | 1/2008 |
| WO | WO 2008/132601 | 11/2008 |
| WO | WO 2008/156712 | 12/2008 |
| WO | WO 2009/044273 | 4/2009 |
| WO | WO 2011/014438 | 2/2011 |
| WO | WO 2011/066389 | 6/2011 |
| WO | WO 2013/006490 | 1/2013 |
| WO | WO 2013/025779 | 2/2013 |
| WO | WO 2013/067492 | 5/2013 |
| WO | WO 2018/009904 | 1/2018 |

OTHER PUBLICATIONS

Sonowal, H., et al., Aldose reductase inhibitor increases doxorubicin-sensitivity of colon cancer cells and decreases cardiotoxicity, Jun. 9, 2017, Nature, 7, 3182 (Year: 2017).*

Tekmal, R., Targeting Aldose Reductase: A Novel Strategy in Treating Endocrine Resistance Using Combination Therapy, Dec. 15, 2009, Cancer Res, 69, (24_Supplement), 67 (Year: 2009).*

Berd, et al.,"Induction of Cell-Mediated Immunity to Autologous Melanoma Cells and Regreesion of Metastases After Treatment with a Melanoma Cell Vaccine Preceded by Cyclophosphamide," *Cancer Research*, 46: 2572-2577, 1986.

Brignone, et al., "A Phase I Pharmacokinetic and Biological Correlative Study of IMP321, A Novel MHC Class II Agonist, in Patients with Advanced Renal Cell Carcinoma," *Clinical Cancer Research*, 15: 6225-6231, 2009.

Hamid, et al., "Safety and Tumor Responses with Lambrolizumab (Anti-PD-1) in Melanoma," *New England Journal of Medicine*, 369: 134-144, 2013.

Hoover, et al., "Prospectively Randomized Trial of Adjuvant Active-Specific Immunotherapy for Human Colorectal Cancer," *Cancer*, 55: 1236-1243, 1985.

International Search Report and Written Opinion Issued in Corresponding PCT Application No. PCT/US2019/019134, dated May 10, 2019.

Jones, et al., "Tim-3 Expression Defines A Novel Population of Dysfunctional T Cells with Highly Elevated Frequencies in Progressive HIV-1 Infection," *Journal of Experimental Medicine*, 205(12): 2763-2779, 2008.

Levin, et al., Human Tumors Short Term Culture Techniques and Clinical Applications, P.P Dendy Ed., Academic Press, London, 277-280, 1976.

Mellman, et al., "Cancer Immunotherapy Comes of Age," *Nature*, 480: 480-489, 2011.

Mkrtichyan, "B7-DC-Ig Enhances Vaccine Effect by a Novel Mechanism Dependent on PD-1 Expression Level on T Cell Subsets," *Journal of Immunology*, 189: 2338-2347, 2012.

Nishimura, et al., "Development of Lupus-Like Autoimmune Diseases by Disruption of the PD-1 Gene Encoding an ITIM Motif-Carrying Immunoreceptor," *Immunity*, 11: 141-151, 1999.

Pardoll, "The Blockade of Immune Checkpoints in Cancer Immunotherapy," *Nature Reviews Cancer*, 12: 252-264, 2012.

Pascolo, "Vaccination with Messenger RNA," *Methods in Molecular Medicine*, 127: 23-40, 2006.

Pfistershammer, et al., "No Evidence for Dualism in Function and Receptors: PD-L2/B7-DC is an Inhibitory Regulator of Human T Cell Activation," *European Journal of Immunology*, 36: 1104-1113, 2006.

Rammensee, et al., "SYFPEITHI: Database for MHC Ligands and Peptide Motifs," *Immunogenetics*, 50: 213-219, 1999.

Restifo & Rosenberg, "Developing Recombinant and Synthetic Vaccines for the Treatment of Melanoma," *Curr Opinion Oncol*, 1: 50-57, 1999.

Ribas, et al., "Phase III Randomized Clinical Trial Comparing Tremelimumab with Standard-of-Care Chemotherapy in Patients with Advanced Melanoma," *Journal of Clinical Oncology*, 31: 616-622, 2013.

Rosenblatt, et al., "PD-1 Blockade by CT-011, Anti-PD-1 Antibody, Enhances Ex Vivo T-Cell Responses to Autologous Dendritic Cell/Myeloma Fusion Vaccine," *Journal of Immunotherapy*, 34: 409-418, 2011.

Topalian, et al., "Safety, Activity, and Immune Correlates of Anti-PD-1 Antibody iin Cancer," *New England Journal of Medicine*, 366: 2443-2454, 2012.

Waterhouse, et al., "Lymphoproliferative Disorders with Early Lethality in Mice Deficient in Ctla-4," *Science*, 270(5238): 985-988, 1995.

Wolchok, et al., "Nivolumab Plus Ipilimumab in Advanced Melanoma," *New England Journal of Medicine*, 369: 122-133, 2013.

Zhu, et al., "The Tim-3 Ligand Galectin-9 Negatively Regulates T Helper Type I Immunity," *Nature Immunology*, 6: 1245-1252, 2005.

* cited by examiner

COMBINATION THERAPY FOR THE TREATMENT OF CANCER

CROSS REFERENCE TO RELATED APPLICATIONS

This Application is a national phase application under 35 U.S.C. § 371 of International Patent Application No. PCT/US2019/019134, filed Feb. 22, 2019, which claims priority to U.S. Provisional Application Ser. No. 62/633,820 filed Feb. 22, 2018, and is incorporated herein by reference in its entirety.

STATEMENT REGARDING FEDERALLY FUNDED RESEARCH

This invention was made with government support under CA129383 awarded by the National Institutes of Health. The government has certain rights in the invention.

BACKGROUND OF THE INVENTION

A. Field of the Invention

The invention generally concerns aldose reductase inhibitor compositions and methods of using these compositions for the treatment of cancer.

B. Description of Related Art

Colorectal cancer (CRC) is the third leading cause of cancer-related deaths in women in the United States and the second leading cause in men, causing approximately 50,000 deaths in 2017. Despite recent advancement in diagnostics and treatments such as surgery, chemotherapy and radiation therapy, the survival rate of colorectal cancer is poor due to recurrence of the disease. Treatment modalities currently being used for metastatic CRC have been shown to have only modest efficacy and are also associated with significant toxicities. This unmet need for effective treatment of metastatic CRC has driven the search for novel strategies to improve survival while minimizing toxicities experienced by patients.

Immunotherapy, one of the most exciting recent developments in cancer therapy, includes cancer vaccines, targeted-therapy, cytokine-therapy, adoptive cell-therapy (ACT) and immune check point inhibitors and has shown promise in treating solid tumors. The FDA approval of immunotherapies such as the cancer vaccine Sipuleucel-T™ and the immune checkpoint inhibitors, ipilimumab, monoclonal antibodies (Abs) which target CTLA-4 (cytotoxic T-lymphocyte-associated protein 4), and nivolumab and pembrolizumab which target Programmed Death 1 (PD-1; CD279) heralds an exciting change in the direction of cancer therapeutics. Clinical trials with mAbs targeting either PD-1 or PD-L1 have shown dramatic responses and long-term regressions in patients with melanoma, renal carcinoma, non-small cell lung cancer, Hodgkin's Lymphoma, and other cancers. Also a number of strategies are being developed to enhance the therapeutic efficacy of PD1/PD-L1 blockade, such as combining it with other anticancer therapies Despite important clinical benefits, these therapies are associated with a diverse spectrum of immune-related adverse events (irAEs) that are usually transient, but rarely severe or fatal Therefore, due to the complex nature of tumorigenesis and modest levels of success of immunotherapies as monotherapy and considering it's irAEs to the patients, a better approach using combination therapy should be developed which can increase the efficacy of immune check point inhibitor as well as reduce the immune mediated side effects of the immunotherapy.

There remains a need for additional immunotherapies and cancer therapies.

SUMMARY OF THE INVENTION

Aspects of the current invention provide a solution to the problems associated with current cancer therapies; in particular, immune checkpoint inhibitor therapies. By way of example, the inventors have discovered a process to enhance the effectiveness of immune checkpoint inhibition therapy. Embodiments are directed to various combination therapies for enhancing anti-cancer effects that include aldose reductase inhibitors and an immunotherapy.

Certain embodiments are directed to methods of treating a subject having cancer comprising, administering (i) a composition comprising an aldose reductase specific inhibitor and (ii) a composition comprising an immunotherapy to the subject having cancer. In certain aspects, the cancer is melanoma, head and neck, bladder, breast, lung, or colorectal cancer. In certain aspects the immunotherapy is an immune checkpoint inhibitor, anti-cancer cell therapy, or an anti-cancer vaccine Certain embodiments are directed to methods of treating a subject having cancer comprising, administering (i) a composition comprising an aldose reductase specific inhibitor and (ii) a composition comprising an immune checkpoint inhibitor to the subject having melanoma, head and neck, or colorectal cancer. In certain aspects the aldose reductase specific inhibitor is selected from ponalrestat, tolrestat, epalrestat, zenarestat, sorbinil, fidarestat, minalrestat, ranirestatin, or zopolrestat. In a particular aspect the aldose reductase specific inhibitor is fidarestat. In certain aspects the immune checkpoint inhibitor is an inhibitor of the PD-1/PD-L1, CTLA4/B7-1, TIM-3, LAG3, B7-He or H4 pathway. In a particular aspect the immune checkpoint inhibitor is an antibody or an antibody segment(s). In a more particular aspect the immune checkpoint inhibitor is an anti-PD1 antibody or binding segment(s) thereof. The aldose reductase specific inhibitor can be administered 5 about 1, 2, 3, 4, 5, 6, 7, 8, 9, or 10 minutes, hours or days prior to administration of the immune checkpoint inhibitor, or vice versa. In certain aspects the aldose reductase inhibitor and immune checkpoint inhibitor are administered simultaneously or substantially simultaneously (e.g., within 10 to 30 minutes of each other). In certain aspects the aldose reductase inhibitor, the immune checkpoint inhibitor or the aldose reductase inhibitor and immune checkpoint inhibitor are administered by injection or intratumoral injection. In certain aspects the cancer is premalignant, malignant, metastatic, or drug-resistant. In a particular aspect, the cancer is bladder cancer, breast cancer, lung cancer, or colorectal cancer.

Other embodiments are directed to anti-cancer compositions comprising an aldose reductase inhibitor and an immune checkpoint inhibitor. In certain aspects the aldose reductase inhibitor is selected from ponalrestat, tolrestat, epalrestat, zenarestat, sorbinil, fidarestat, minalrestat, ranirestatin, or zopolrestat. In a particular aspect, the aldose reductase inhibitor is fidarestat. In certain aspects the immune checkpoint inhibitor is an inhibitor of the PD-1/PD-L1, CTLA4/B7-1, TIM-3, LAG3, B7-He or H4 pathway. In certain instances, the immune checkpoint inhibitor is an antibody or an antibody segment(s). In particular aspects the immune checkpoint inhibitor is an anti-PD1 antibody or binding segment(s) thereof.

In other embodiments, AR expression can be negatively modulated in conjunction with administration of immune checkpoint inhibitor(s). Negative regulation of gene expression, including modulation of gene transcription and/or mRNA translation.

An "immune checkpoint inhibitor" is a molecule that directly or indirectly inhibits, partially or completely, an immune checkpoint pathway. Without wishing to be bound by any particular theory, it is generally thought that immune checkpoint pathways function to turn on or off aspects of the immune system, particularly T cells. Following activation of a T cell, a number of inhibitory receptors can be upregulated and present on the surface of the T cell in order to suppress the immune response at the appropriate time. In the case of persistent immune stimulation immune checkpoint pathways can suppress the immune response and lead to immune exhaustion. Examples of immune checkpoint pathways include, without limitation, PD-1/PD-L1, CTLA4/B7-1, TIM-3, LAG3, By-He, H4, HAVCR2, ID01, CD276 and VTCN1. In the instance of the PD-1/PD-L1 immune checkpoint pathway, an inhibitor may bind to PD-1 or to PD-L1 and prevent interaction between the receptor and ligand. Therefore, the inhibitor may be an anti-PD-1 antibody or anti-PD-L1 antibody. Similarly, in the instance of the CTLA4/B7-1 immune checkpoint pathway, an inhibitor may bind to CTLA4 or to B7-1 and prevent interaction between the receptor and ligand. Non-limiting examples of immune checkpoint inhibitors include fully human monoclonal antibodies, such as BMS-936558/MDX-1106, BMS-936559/MDX-1105, ipilimumab/Yervoy, and tremelimumab; humanized antibodies, such as CT-011 and MK-3475; and fusion proteins, such as AMP-224.

The terms "combination therapy" or "combined treatment" or "in combination" as used herein denotes any form of concurrent or parallel treatment with at least two distinct therapeutic agents.

The terms "short interfering nucleic acid," "siNA" or SINA" molecules, "short interfering RNA," "siRNA," "short interfering nucleic acid molecule," "short interfering oligonucleotide molecule," as used herein, refer to any nucleic acid molecule capable of inhibiting or down-regulating gene expression by an RNA interference mechanism.

The term "RNA" as used herein means a molecule comprising at least one ribonucleotide residue and includes double stranded RNA, single stranded RNA, isolated RNA, partially purified, pure or synthetic RNA, recombinantly produced RNA, as well as altered RNA or analogs of naturally occurring RNA.

The term "target nucleic acid" as used herein means any nucleic acid sequence whose expression or activity is to be modulated. The target nucleic acid can be DNA or RNA.

The term "sense region" as used herein means a nucleotide sequence of a siNA molecule having the same sequence as a target nucleic acid sequence. In addition, the sense region of a siRNA molecule can comprise a nucleic acid sequence having complementarity to a antisense region of the siNA molecule.

The term "antisense region" as used herein means a nucleotide sequence of a siRNA molecule having complementarity to a target nucleic acid sequence. The term can also encompass a nucleic acid sequence having complementarity to a sense region of the siRNA molecule.

The term "complementarity" as used herein means that the nucleic acid can form hydrogen bonds with another nucleic acid molecule (e.g. A-T, A-U, G-C).

The term "modulate" as used herein means that the expression of the gene or level of RNA molecule or equivalent RNA molecules encoding one or more protein or protein subunits, or activity of one or more protein subunits, is up-regulated or down-regulated such that the expression, level or activity is greater than or less than that observed in the absence of the modulator. The term "modulate" encompasses "inhibit" but the use of the terms is not limited in this definition.

The term "gene" as used herein means a nucleic acid that encodes a RNA sequence including but not limited to structural genes encoding a polypeptide. In particular the gene encodes aldose reductase.

"Administering" or "administration" or "administer" means providing a material to a subject in a manner that is pharmacologically useful. The term includes causing to be administered. "Causing to be administered" means causing, urging, encouraging, aiding, inducing or directing, directly or indirectly, another party to administer the material.

"Amount effective" or "effective amount" is any amount of a composition provided herein that produces one or more desired responses, such as one or more desired immune responses, including a reduced immunosuppressive immune response against a cancer. For in vivo purposes, the amount can be one that a clinician would believe may have a clinical benefit for a subject in need. An effective amount that a clinician would believe may have a clinical benefit for such a subject is also referred to herein as a "clinically effective amount".

An "effective amount" of an anti-cancer agent in reference to decreasing cancer cell growth, means an amount capable of decreasing, to some extent, the growth of some cancer or tumor cells. The term includes an amount capable of invoking a growth inhibitory, cytostatic and/or cytotoxic effect and/or apoptosis of the cancer or tumor cells.

A "therapeutically effective amount" in reference to the treatment of cancer, means an amount capable of invoking one or more of the following effects: (1) inhibition, to some extent, of cancer or tumor growth, including slowing down growth or complete growth arrest; (2) reduction in the number of cancer or tumor cells; (3) reduction in tumor size; (4) inhibition (i.e., reduction, slowing down, or complete stopping) of cancer or tumor cell infiltration into peripheral organs; (5) inhibition (i.e., reduction, slowing down, or complete stopping) of metastasis; (6) enhancement of anti-tumor immune response, which may, but is not required to, result in the regression or rejection of the tumor, or (7) relief, to some extent, of one or more symptoms associated with the cancer or tumor. The therapeutically effective amount may vary according to factors such as the disease state, age, sex and weight of the individual and the ability of one or more anti-cancer agents to elicit a desired response in the individual. A "therapeutically effective amount" is also one in which any toxic or detrimental effects are outweighed by the therapeutically beneficial effects.

The phrases "treating cancer" and "treatment of cancer" mean to decrease, reduce, or inhibit the replication of cancer cells; decrease, reduce or inhibit the spread (formation of metastases) of cancer; decrease tumor size; decrease the number of tumors (i.e. reduce tumor burden); lessen or reduce the number of cancerous cells in the body; prevent recurrence of cancer after surgical removal or other anti-cancer therapies; or ameliorate or alleviate the symptoms of the disease caused by the cancer.

Subjects include, in some embodiments, those that have or are at risk of having cancer, in particular colorectal cancer.

As used herein, an "inhibitor" can be any chemical compound, peptide, or polypeptide that can reduce the activity or function of a protein, in particular embodiment the inhibitor is a small molecule inhibitor. Direct inhibition can be accomplished, for example, by binding to a protein and thereby preventing the protein from binding an intended target, such as a receptor, or by inhibiting an enzymatic or other activity of the protein, either competitively, non-competitively, or uncompetitively. Indirect inhibition can be accomplished, for example, by binding to a protein's intended target, such as a receptor or binding partner, thereby blocking or reducing activity of the protein.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard error of mean for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain embodiments or aspects of the present invention. The invention may be better understood, but not limited by reference to one or more of these drawings in combination with the detailed description of the specification embodiments presented herein.

DETAILED DESCRIPTION OF THE INVENTION

Figure 1:
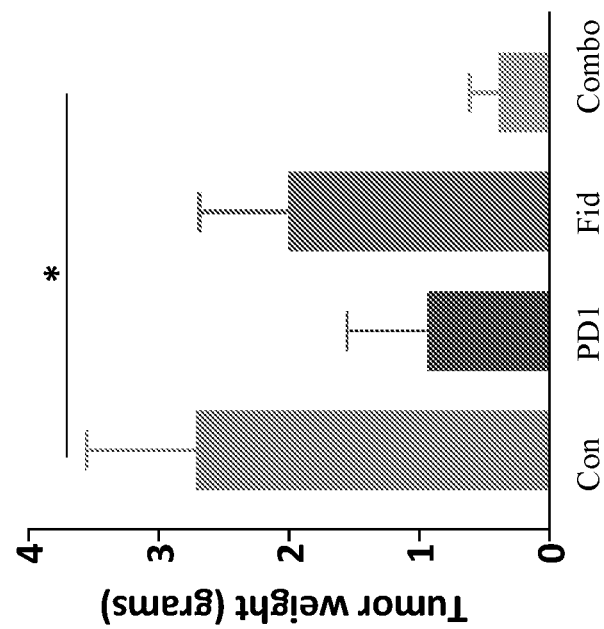
FIG. 1A-1B: Fidarestat increases the therapeutic potential of anti-PD1 in CT-26 syngeneic mouse models. CT-26 cells ($0.5 \times 10^6$) were injected subcutaneously into the flanks of Balb/c mice (n=4-7) on day 0. When tumor volume reaches approximately 45 $mm^3$, the mice were injected (i.p.) anti-PD-1, 200 µg/mouse, twice per week. Aldose reductase inhibitor (ARI) (25 mg/kg/day) were given in drinking water or by gavage. CT26 tumor were left untreated (Con) or treated with fidarestat (Fid), anti-PD-1 (PD1) or combination of both (Combo). Con mice were also treated with isotype matched control antibodies (PD-1 iso). Tumor growth was measured twice per week and animals were euthanized when the tumor volume reaches 2000 $mm^3$ in the control mice (~30 days). Tumor volume (A) and tumor weight (B) were measured. Data Mean S.E.M. $P<0.05$; $*P<0.05$; $**P<0.01$ by one-way ANOVA followed by Dunnet and Tukey's multiple comparison test.
Figure 1:
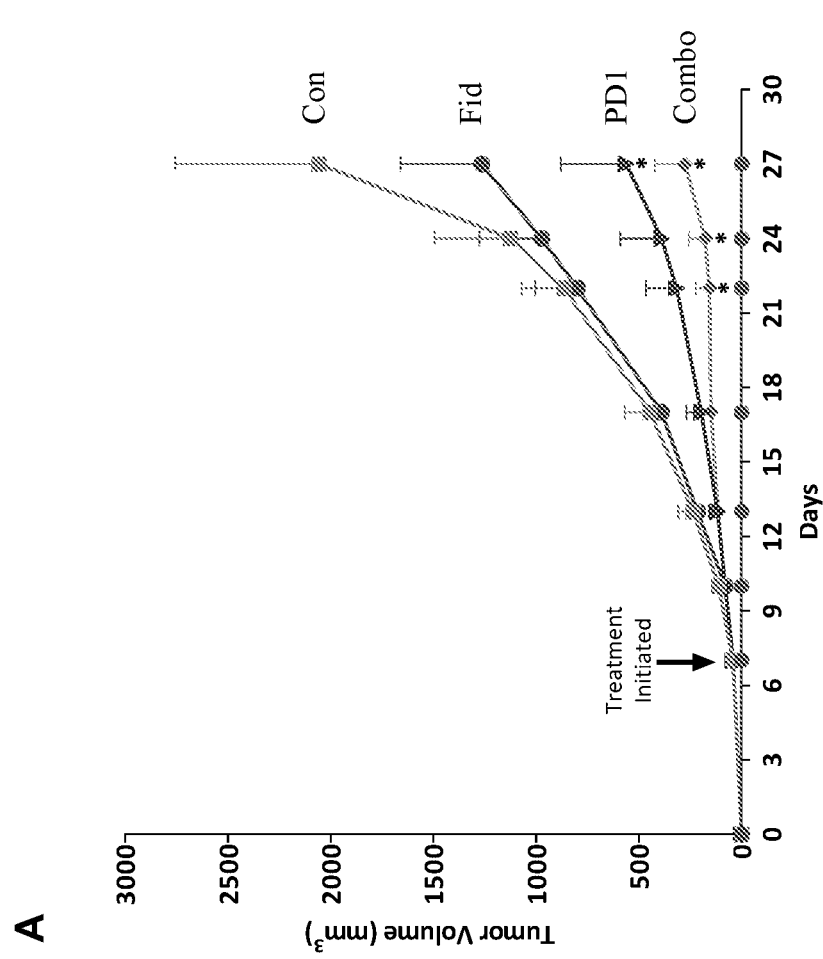

In the treatment of challenging diseases, such as cancer, generation of immune responses to tumor-related antigens is often difficult due to the complexity of the immune response and the presence of multiple refractory or immunosuppressive pathways that prevent generation of a robust immune response.

The inventors' studies with the polyol pathway enzyme, aldose reductase (AR; AKR1B1) have shown AR inhibition by fidarestat, a compound that has undergone a Phase-III clinical trial for the treatment of diabetic nephropathy and found to have no major side effects, increased the sensitivity of colorectal cancer cells to doxorubicin and prevented cardiotoxicity associated with the effective and relatively inexpensive synthetic anthracycline drugs. The inventors have also shown that AR inhibition prevents colorectal cancer cells growth in tissue culture, nude mouse xenografts, and chemically-induced animal models of colorectal cancer. Based on these studies, the inventors investigated whether an AR inhibitor such as fidarestat could be used as combination therapy along with immune checkpoint inhibitor such as an anti-PD1 antibody resulting in an increase in the immunotherapeutic efficacy of anti-PD1 and prevent CRC growth. The results are very exciting; using syngeneic colorectal cancer model, the inventors observe that fidarestat increases the efficacy of anti-PD1 via regulating CD8 T and NK cells and their effector function, and MDSCs, which in turn regress the tumor significantly.

Certain embodiments are directed to methods of treating cancer and symptoms thereof by administering an aldose reductase inhibitor in combination with an immune checkpoint inhibitor. In yet other related embodiments there is provided a method of treating colorectal cancer in a subject, comprising administering a pharmacologically effective amount of an aldose reductase inhibitor to the subject to inhibit colorectal cancer cell proliferation thereby treating the colorectal cancer.

A. Aldose Reductase Inhibitors

The inhibitors of aldose reductase can be any compound that inhibits the enzyme aldose reductase. It is contemplated that the aldose reductase inhibitors provided herein may be used as a therapeutic to treat cancer or symptoms thereof. The aldose reductase inhibitor compounds of this invention are readily available or can be easily synthesized by those skilled in the art using conventional methods of organic synthesis. A number of aldose reductase inhibitors are known, for example (2S,4S)-6-fluoro-2',5'-dioxospiro(chroman-4,4'-imidazolidine)-2-carboxamide (fidarestat, U.S. Pat. No. 5,447,946); 3-(4-bromo-2-fluorobenzyl)-3,4-dihydro-4-oxo-1-phthalazineacetic acid (ponalrestat, U.S. Pat. No. 4,251,528); N[[(5-trifluoromethyl)-6-methoxy-1-naphthalenyl]thioxomethyl]-N-methylglycine (tolrestat, U.S. Pat. No. 4,600,724); 5-[(Z,E)-β-methylcinnamylidene]-4-oxo-2-thioxo-3-thiazolideneacetic acid (epalrestat, U.S. Pat. Nos. 4,464,382, 4,791,126, and 4,831,045); 3-(4-bromo-2-fluorobenzyl)-7-chloro-3,4-dihydro-2,4-dioxo-1(2H)-quinazolineacetic acid (zenarestat, U.S. Pat. Nos. 4,734,419, and 4,883,800); 2R,4R-6,7-dichloro-4-hydroxy-2-methyl-chroman-4-acetic acid (U.S. Pat. No. 4,883,410); 2R,4R-6, 7-dichloro-6-fluoro-4-hydroxy-2-methylchroman-4-acetic acid (U.S. Pat. No. 4,883,410); 3,4-dihydro-2,8-diisopropyl-3-oxo-2H-1,4-benzoxazine-4-acetic acid (U.S. Pat. No. 4,771,050); 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,572); N-[3,5-dimethyl-4-[(nitromethyl)sulfonyl]phenyl]-2-methyl-benzeneacetamide (ZD5522, U.S. Pat. Nos. 5,270,342 and 5,430,060); (S)-6-fluorospiro[chroman-4,4'-imidazolidine]-2,5'-dione (sorbinil, U.S. Pat. No. 4,130,714); d-2-methyl-6-fluoro-spiro (chroman-4',4'-imidazolidine)-2',5'-dione (U.S. Pat. No. 4,540,704); 2-fluoro-spiro(9H-fluorene-9,4'-imidazolidine)-2',5'-dione (U.S. Pat. No. 4,438,272); 2,7-di-fluoro-spiro (9H-fluorene-9,4'-imidazolidine)-2',5'-dione (U.S. Pat. Nos. 4,436,745, 4,438,272); 2,7-di-fluoro-5-methoxy-spiro(9H-fluorene-9,4'-imidazolidine)-2',5'-dione (U.S. Pat. Nos. 4,436,745, 4,438,272); 7-fluoro-spiro(5H-indenol[1,2-b] pyridine-5,3'-pyrrolidine)-2,5'-dione (U.S. Pat. Nos. 4,436, 745, 4,438,272); d-cis-6'-chloro-2',3'-dihydro-2'-methyl-spiro-(imidazolidine-4,4'-4'H-pyrano(2,3-b)pyridine)-2,5-dione (U.S. Pat. No. 4,980,357); spiro[imidazolidine-4,5' (6H)-quinoline]-2,5-dione-3'-chloro-7',8'-dihydro-7'-methyl-(5'-cis) (U.S. Pat. No. 5,066,659); and 2-[(4-bromo-2-fluorophenyl)methyl]-6-fluorospiro[isoquinoline-4(1H), 3'-pyrrolidine]-1,2',3,5'(2H)-tetrone (minalrestat, U.S. Pat. No. 5,037,831). Moreover, in other embodiments it is specifically contemplated that any of these may be excluded as part of the invention.

It is standard in the art to formulate a therapeutic compound with a pharmaceutically acceptable carrier as a pharmaceutical composition. It is also standard in the art to determine dose, dosage and routes of administration of the therapeutic or pharmaceutical compounds. Such determination is routinely made by one of skill in the art based on the individual and the particular pathophysiological state or symptoms exhibited by the patient and the patients history.

In certain embodiments, the expression of AR is negatively modulated in conjunction with immune checkpoint inhibition.

Various molecules can be modulators of the activity or expression of a gene or gene product that modulates activity of the AR protein or pathway. In some embodiments, molecules that inhibit expression of AR are short double stranded (ds) nucleic acid molecules, such as dsRNA molecules, which may operate via RNA interference (RNAi).

The term "interfering RNA" or "RNAi" or "interfering RNA sequence" refers to double-stranded RNA (i.e., duplex RNA) that targets (i.e., silences, reduces, or inhibits) expression of a target gene (i.e., by mediating the degradation of mRNAs which are complementary to the sequence of the interfering RNA) when the interfering RNA is in the same cell as the target gene. Interfering RNA thus refers to the double stranded RNA formed by two complementary strands or by a single, self-complementary strand. Interfering RNA typically has substantial or complete identity to the target gene. The sequence of the interfering RNA can correspond to the full length target gene, or a subsequence thereof. Interfering RNA includes small-interfering RNA" or "siRNA," i.e., interfering RNA of about 15-60, 15-50, 15-50, or 15-40 (duplex) nucleotides in length, more typically about, 15-30, 15-25 or 19-25 (duplex) nucleotides in length, and is preferably about 20-24 or about 21-22 or 21-23 (duplex) nucleotides in length (e.g., each complementary sequence of the double stranded siRNA is 15-60, 15-50, 15-50, 15-40, 15-30, 15-25 or 19-25 nucleotides in length, preferably about 20-24 or about 21-22 or 21-23 nucleotides in length, and the double stranded siRNA is about 15-60, 15-50, 15-50, 15-40, 15-30, 15-25 or 19-25 preferably about 20-24 or about 21-22 or 21-23 base pairs in length). siRNA duplexes may comprise 3' overhangs of about 1 to about 4 nucleotides, preferably of about 2 to about 3 nucleotides and 5' phosphate termini. The siRNA can be chemically synthesized or maybe encoded by a plasmid (e.g., transcribed as sequences that automatically fold into duplexes with hairpin loops). siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., *PNAS USA* 99: 9942-7 (2002); Calegari et al., *PNAS USA* 99: 14236 (2002); Byrom et al., *Ambion Tech-Notes* 10(1): 4-6 (2003); Kawasaki et al., *Nucleic Acids Res.* 31: 981-7 (2003); Knight and Bass, Science 293: 2269-71 (2001); and Robertson et al., *J. Biol. Chem.* 243: 82 (1968)). Preferably, dsRNA are at least 50 nucleotides to about 100, 200, 300, 400 or 500 nucleotides in length. A dsRNA may be as long as 1000, 1500, 2000, 5000 nucleotides in length, or longer. The dsRNA can encode for an entire gene transcript or a partial gene transcript.

Although the dsRNA contains a sequence which corresponds to the target region of the (target) gene (e.g., AR) it is not absolutely essential for the whole of the dsRNA to correspond to the sequence of the target region. For example, the dsRNA may contain short non-target regions flanking the target-specific sequence, provided that such sequences do not affect performance of the dsRNA in RNA inhibition to a material extent.

The expression "target region" or "target nucleotide sequence" of the (target) gene may be any suitable region or nucleotide sequence of the gene. The target region should comprise at least 17, at least 18 or at least 19 consecutive nucleotides of the (target) gene, more preferably at least 20 or at least 21 nucleotide and still more preferably at least 22, 23 or 24 nucleotides of the (target) gene.

The dsRNA may contain one or more substitute bases in order to optimize performance in RNAi. It will be apparent to the skilled person how to vary each of the bases of the dsRNA in turn and test the activity of the resulting siRNAs (e.g. in a suitable in vitro test system) in order to optimize the performance of a given dsRNA.

The dsRNA may further contain DNA bases, non-natural bases or non-natural backbone linkages or modifications of the sugar-phosphate backbone, for example, to enhance stability during storage or enhance resistance to degradation by nucleases.

It has been suggested that synthetic RNA duplexes consisting of either 27-mer blunt or short hairpin (sh) RNAs with 29 bp stems and 2-nt 3' overhangs are more potent inducers of RNA interference than conventional 21-mer siRNAs. Thus, molecules based upon the targets identified above and being either 27-mer blunt or short hairpin (sh) RNAs with 29-bp stems and 2-nt 3' overhangs are also included within the scope of the invention.

The double-stranded RNA may be fully or partially double-stranded. Partially double-stranded RNAs may include short single-stranded overhangs at one or both ends of the double-stranded portion, provided that the RNA is still capable of being taken up by the cell and directing RNAi. The double-stranded RNA may also contain internal non-complementary regions.

Thus, the invention also features the use of small nucleic acid molecules, including antisense nucleic acids and short interfering nucleic acid (siNA), the latter include, for example: microRNA (miRNA), short interfering RNA (siRNA), double-stranded RNA (dsRNA), and short hairpin RNA (shRNA) molecules to knockdown expression of proteins such as AR. An siNA of the invention can be unmodified or chemically-modified. An siNA of the instant invention can be chemically synthesized, expressed from a vector or enzymatically synthesized. The instant invention also features various chemically-modified synthetic short interfering nucleic acid (siNA) molecules capable of modulating gene expression or activity in cells by RNA interference (RNAi). The use of chemically-modified siNA improves various properties of native siNA molecules through, for example, increased resistance to nuclease degradation in vivo and/or through improved cellular uptake. Furthermore, siNA having multiple chemical modifications may retain its RNAi activity. The siNA molecules of the instant invention provide useful reagents and methods for a variety of therapeutic applications. In some embodiments the AR expression inhibitors are used for treating cancer or enhancing the effectiveness of immune check point inhibitors and their target pathways.

Chemically synthesizing nucleic acid molecules with modifications (base, sugar and/or phosphate) that prevent their degradation by serum ribonucleases can increase their potency (see e.g., Eckstein et al., International Publication No. WO 92/07065; Perrault et al, 1990 *Nature* 344, 565; Pieken et al., 1991, *Science* 253, 314; Usman and Cedergren, 1992, *Trends in Biochem. Sci.* 17, 334; Usman et al., International Publication No. WO 93/15187; and Rossi et al., International Publication No. WO 91/03162; Sproat, U.S. Pat. No. 5,334,711; all of these describe various chemical modifications that can be made to the base, phosphate and/or sugar moieties of the nucleic acid molecules herein). Modifications which enhance their efficacy in cells, and removal of bases from nucleic acid molecules to shorten oligonucleotide synthesis times and reduce chemical requirements are desired.

In one embodiment, one of the strands of the double-stranded siNA molecule comprises a nucleotide sequence that is complementary to a nucleotide sequence of a target RNA (e.g., AR mRNA) or a portion thereof, and the second strand of the double-stranded siNA molecule comprises a nucleotide sequence identical to the nucleotide sequence or a portion thereof of the targeted RNA. In another embodiment, one of the strands of the double-stranded siNA molecule comprises a nucleotide sequence that is substantially complementary to a nucleotide sequence of a target RNA or a portion thereof, and the second strand of the double-stranded siNA molecule comprises a nucleotide sequence substantially similar to the nucleotide sequence or a portion thereof of the target RNA. In another embodiment, each strand of the siNA molecule comprises about 19 to about 23 nucleotides, and each strand comprises at least about 19 nucleotides that are complementary to the nucleotides of the other strand.

In some embodiments an siNA is an shRNA, shRNA-mir, or microRNA molecule encoded by and expressed from a genomically integrated transgene or a plasmid-based expression vector. Thus, in some embodiments a molecule capable of inhibiting mRNA expression, or microRNA activity, is a transgene or plasmid-based expression vector that encodes a small-interfering nucleic acid. Such transgenes and expression vectors can employ either polymerase II or polymerase III promoters to drive expression of these shRNAs and result in functional siRNAs in cells. The former polymerase permits the use of classic protein expression strategies, including inducible and tissue-specific expression systems. In some embodiments, transgenes and expression vectors are controlled by tissue specific promoters. In other embodiments transgenes and expression vectors are controlled by inducible promoters, such as tetracycline inducible expression systems.

In another embodiment, a small interfering nucleic acid of the invention is expressed in mammalian cells using a mammalian expression vector. The recombinant mammalian expression vector may be capable of directing expression of the nucleic acid preferentially in a particular cell type (e.g., tissue-specific regulatory elements are used to express the nucleic acid). Tissue specific regulatory elements are known in the art. Non-limiting examples of suitable tissue-specific promoters include the myosin heavy chain promoter, albumin promoter, lymphoid-specific promoters, neuron specific promoters, pancreas specific promoters, and mammary gland specific promoters. Developmentally-regulated promoters are also encompassed, for example the murine hox promoters and the alpha-fetoprotein promoter.

The terms "knockdown of gene expression", "inhibition of gene expression" and the like are used interchangeably and refer to a measurable or observable reduction in gene expression or a complete abolition of detectable gene expression, at the level of protein product and/or mRNA product from the (target) gene. Knockdown or inhibition of gene expression is "specific" when knockdown or inhibition of the (target) gene occurs without manifested effects on other genes of the targeted cell or organism. The term "knockdown of gene expression" implies reduced expression of one or more genes of an organism due to the action of a dsRNA such as a short DNA or RNA oligonucleotide with a sequence complementary to a gene or its mRNA transcripts. During a gene knockdown event, the binding of this dsRNA to the gene or its transcripts causes decreased expression through blocking of transcription.

Depending on the nature of the affected gene, knockdown or inhibition of gene expression in cells can be confirmed by phenotypic analysis of a cell or by measurement of mRNA or protein expression using molecular techniques such as RNA solution hybridization, nuclease protection, Northern hybridization, reverse transcription polymerase chain reaction, gene expression monitoring with a microarray, antibody binding, enzyme-linked immunosorbent assay (ELISA), Western blotting, radioimmunoassay (RIA), other immunoassays, or fluorescence-activated cell analysis (FACS).

B. Cancer Immunotherapies

Cancer immunotherapy is the targeting or use of immune system components to kill cancer cells and can include antibodies, vaccines, and T cells. Cancer immunotherapies trigger or modulate the body's own immune system to find and destroy neoplastic cells. Natural killer T cells (NKT) and γδ T cells have been identified as critical components in cancer immunosurveillance. The initial success of preclinical trials in the last decades has evoked NKT or γδ T cells based immunotherapeutic approaches for the treatment of cancer. Currently different nonspecific immunotherapies are used to stimulate the immune system to improve or induce an immune response against neoplastic cells. Nonspecific immunotherapy refers to therapies that can stimulate the immune system by using a substance that activates or enhances immune cell function regardless of their antigen specificity. Nonspecific immunotherapies known in the art include, for example, Bacille Calmette-Guerin (BCG) therapy, cytokine therapy, cell therapy etc. In certain aspects, the cancer immunotherapy includes specific or non-specific immunotherapies such as immune checkpoint inhibitors, cell therapy, and/or vaccines.

1. Immune Checkpoint Inhibitors

The term "immune checkpoint protein" is known in the art. Within the known meaning of this term it will be clear to the skilled person that on the level of "immune checkpoint proteins" the immune system provides inhibitory signals to its components in order to balance immune reactions. Known immune checkpoint proteins may comprise CTLA-4, PD1 and its ligands PD-L1 and PD-L2 and in addition LAG-3, BTLA, B7H3, B7H4, TIM3, MR. The pathways involving LAG3, BTLA, B7H3, B7H4, TIM3, and MR are recognized in the art to constitute immune checkpoint pathways similar to the CTLA-4 and PD-1 dependent pathways (see e.g. Pardoll, 2012. *Nature Rev Cancer* 12:252-264; Mellman et al., 2011. *Nature* 480:480-489).

Within the present invention an immune checkpoint inhibitor is any compound inhibiting the function of an immune checkpoint protein. Inhibition includes reduction of function and full blockade. In particular the immune checkpoint protein is a human immune checkpoint protein. Thus, the immune checkpoint inhibitor preferably is an inhibitor of a human immune checkpoint protein. The designation immune checkpoint includes the experimental demonstration of stimulation of an antigen-receptor triggered T lymphocyte response by inhibition of the immune checkpoint protein in vitro or in vivo, e.g., mice deficient in expression of the immune checkpoint protein demonstrate enhanced antigen-specific T lymphocyte responses or signs of autoimmunity (such as disclosed in Waterhouse et al., 1995. *Science* 270:985-988; Nishimura et al., 1999. *Immunity* 11:141-151). It may also include demonstration of inhibition of antigen-receptor triggered CD4+ or CD8+ T cell responses due to deliberate stimulation of the immune checkpoint protein in vitro or in vivo (e.g. Zhu et al., 2005. *Nature Immunol.* 6:1245-1252).

Immune checkpoint inhibitors include antibodies that specifically recognize immune checkpoint proteins. A number of CTLA-4, PD1, PD-L1, PD-L2, LAG-3, BTLA, B7H3, B7H4, TIM3 and MR inhibitors are known and in analogy of these known immune checkpoint protein inhibitors, alternative immune checkpoint inhibitors may be developed in the (near) future. For example, ipilimumab is a fully human CTLA-4 blocking antibody presently marketed under the name Yervoy (Bristol-Myers Squibb). A second CTLA-4 inhibitor is tremelimumab (referenced in Ribas et al., 2013, *J Clin. Oncol.* 31:616-22). Examples of PD-1 inhibitors include without limitation humanized antibodies blocking human PD-1 such as lambrolizumab (e.g. disclosed as hPD109A and its humanized derivatives h409A11, h409A16 and h409A17 in PCT publication WO2008/156712; Hamid et al., *N Engl. J. Med.* 369: 134-144 2013,), or pidilizumab (disclosed in Rosenblatt et al., 2011. *J Immunother.* 34:409-18), as well as fully human antibodies such as nivolumab (previously known as MDX-1106 or BMS-936558, Topalian et al., 2012. *N Eng. J. Med.* 366:2443-2454, disclosed in U.S. Pat. No. 8,008,449). Other PD-1 inhibitors may include presentations of soluble PD-1 ligand including without limitation PD-L2 Fc fusion protein also known as B7-DC-Ig or AMP-244 (disclosed in Mkrtichyan et al. *J Immunol.* 189:2338-47 2012) and other PD-1 inhibitors presently under investigation and/or development for use in therapy. In addition, immune checkpoint inhibitors may include without limitation humanized or fully human antibodies blocking PD-L1 such as MEDI-4736 (disclosed in PCT publication WO2011/066389), MPDL3280A (disclosed in U.S. Pat. No. 8,217,149) and MIH1 (Affymetrix) and other PD-L1 inhibitors presently under investigation. According to this invention an immune checkpoint inhibitor is preferably selected from a CTLA-4, PD-1 or PD-L1 inhibitor, such as selected from the known CTLA-4, PD-1 or PD-L1 inhibitors mentioned above (ipilimumab, tremelimumab, labrolizumab, nivolumab, pidilizumab, AMP-244, MEDI-4736, MPDL3280A, MIH1). Known inhibitors of these immune checkpoint proteins may be used as such or analogs may be used, in particular chimerized, humanized or human forms of antibodies.

As the skilled person will know, alternative and/or equivalent names may be in use for certain antibodies mentioned above. Such alternative and/or equivalent names are interchangeable in the context of the present invention. For example, it is known that lambrolizumab is also known under the alternative and equivalent names MK-3475 and pembrolizumab.

Certain aspects an immune checkpoint inhibitor is selected from PD1 and PD-L1 inhibitors, such as a known PD-1 or PD-L1 inhibitor mentioned above. In particular embodiments, the PD1 inhibitor is nivolumab or pembrolizumab or another antagonist antibody against human PD1.

The invention also includes the selection of other immune checkpoint inhibitors that are known in the art to stimulate immune responses. This includes inhibitors that directly or indirectly stimulate or enhance antigen-specific T-lymphocytes. These other immune checkpoint inhibitors include, without limitation, agents targeting immune checkpoint proteins and pathways involving PD-L2, LAG3, BTLA, B7H4 and TIM3. For example, human PD-L2 inhibitors known in the art include MIH18 (disclosed in (Pfistershammer et al., 2006. *Eur J Immunol.* 36:1104-13). Another example, LAG3 inhibitors known in the art include soluble LAG3 (I P321, or LAG3-Ig disclosed in PCT publication WO 2009/044273, and in Brignon et al. 2009. *Clin. Cancer Res.* 15:6225-6231) as well as mouse or humanized antibodies blocking human LAG3 (for instance IMP701 disclosed in and derived from PCT publication WO 2008/132601), or fully human antibodies blocking human LAG3 (such as disclosed in European Patent Publication 2320940). Another example is provided by the use of blocking agents towards BTLA, including without limitation antibodies blocking human BTLA interaction with its ligand (such as 4C7 disclosed in PCT publication WO 2011/014438). Yet another example is provided by the use of agents neutralizing B7H4 including without limitation antibodies to human B7H4 (disclosed in PCT publication WO 2013/025779, and in WO 2013/067492) or soluble recombinant forms of B7H4 (such as disclosed in US 20120177645 or Anti-human B7H4 clone H74). Yet another example is provided by agents neutralizing B7-H3, including without limitation antibodies neutralizing human B7-H3 (e.g. MGA271 disclosed as BRCA84D and derivatives in US 20120294796). Yet another example is provided by agents targeting TIM3, including without limitation antibodies targeting human TIM3 (e.g. as disclosed in WO 2013/006490 or the anti-human TIM3, blocking antibody F38-2E2 disclosed by Jones et al., *J Exp Med.* 2008 Nov. 24; 205(12):2763-79). Known inhibitors of immune checkpoint proteins may be used in their known form or analogs may be used, in particular chimerized forms of antibodies, most preferably humanized forms.

The invention also includes the selection of more than one immune checkpoint inhibitor, i.e., more than one pathway can be targeted or a composition can contain immune checkpoint inhibitors that act on the same or different pathways. In certain aspects, the one or more immune checkpoint inhibitor can be selected from CTLA-4, PD-1 or PDL1 inhibitors for combination with an anti-human CD27 agonistic antibody within the various aspects of the invention. For example, concurrent therapy of ipilimumab (anti-CTLA4) with Nivolumab (anti-PD1) has demonstrated clinical activity that appears to be distinct from that obtained in monotherapy (Wolchok et al., 2013, *N. Eng. J. Med.,* 369:122-33).

2. Anti-Cancer Cell Therapy or Vaccines

Antigen-specific immunotherapy refers to either adoptive transfer or vaccination. Adoptive transfer means the direct transfer of the actual components of the immune system that are already capable of producing a specific immune response, such as, for example, T cells or dendritic cells into the recipient. For example, isolated antigen-specific T cells from a cancer patient are expanded to large numbers in vitro, and re-infused back into the patient. Vaccination on the other hand involves the administration of one or more particular antigen(s) to induce a specific immune response by the host (patient).

An active immunotherapy of the invention may be any immunotherapy that stimulates the intrinsic immune system of the recipient, non-specifically, antigen-specifically and/or multi-targeted. Preferably the active immunotherapy is a multi-targeted, antigen-specific immunotherapy. In a preferred embodiment the method of the invention comprises an active immunotherapy, whereby at least one vaccine is administered to the mammal in combination with an aldose reductase inhibitor.

In whole-cell vaccines, the tumor cell itself is used to provide the broadest set of tumor-related antigens. The tumor cells in the composition should contain antigens that are also present in the tumor to be treated, so that the immune response elicited against the antigens in the composition is effected against the tumor. Generally, the cells are recovered from tumors, suspended in a preservation medium and frozen until used for the vaccine preparation. When needed, the cells are thawed, and then stored at temperatures ranging from about 0° C. (on ice) to room temperature until administration. Immunotherapy approaches using unmodified intact tumor cells prepared from tumors taken from the patient, i.e., autologous tumor cells, have been described in the literature (see, e.g., Berd et al., *Cancer Research* 1986; 46:2572-2577; Hoover et al., *Cancer* 1985; 55: 1236-1243; and U.S. Pat. No. 5,484,596).

Alternative vaccine compositions based on disrupted cells have also been suggested including, e.g., tumor membranes (see, e.g., Levin et al., In: Human Tumors in Short Term Culture Techniques and Clinical Applications, P. P. Dendy, Ed., 1976, Academic Press, London, pp. 277-280) or tumor peptides extracted from tumors (see, e.g., U.S. Pat. Nos. 5,550,214 and 5,487,556). The tumor cells can also be modified in some manner to alter or increase the immune response One particular form of tumor cell modification that has a pronounced effect on immunotherapy is coupling of a hapten to the tumor cells. Such haptenized vaccines are described, for example, in WO 96/40173, WO 00/09140, and U.S. Pat. No. 6,333,028. Transducing the tumor with genes so that the tumor cell may act like an antigen-presenting cell or may attract and stimulate local antigen-presenting cells are two approaches.

In another embodiment the cell based vaccine employs non-tumor cells. The cells used for vaccination are antigen presenting cells (APCs), which may be isolated from the patient. These are loaded or pulsed with a tumor antigen ex vivo. The transfer of these pulsed APCs into the patient elicits a significant tumor-specific immune response that attacks the tumor cells. Currently, there are three different methods for pulsing or loading APCs. First, growing APCs in the presence of a tumor-associated protein; second, using genetic engineering techniques to introduce the gene that codes for a tumor-associated protein into APCs, and third, pulsing APCs with fragments (peptides) isolated from a tumor antigen or synthetic peptides. Certain embodiments of the present invention are directed to methods using a vaccine that comprises cells or cellular extracts, such as tumors cells or extracts thereof, which were derived from the same or a different mammal as the one to be treated by the inventive method. The cells are, for example, modified or unmodified tumor cells or APCs loaded or transfected with tumor antigen(s). The tumor antigen that is loaded or transfected includes the same proteins, nucleic acids and/or peptides that may be employed for direct vaccination (see below). The cells may also be T cells for adoptive transfer.

A trimolecular complex consisting of the components of T-cell-antigen receptor, an MHC (Major Histocompatibility Complex) molecule and the ligand thereof, which is a peptide fragment derived from a protein, plays a central role in the regulation of the specific (adaptive) immune response. MHC class I and class II molecules (or the corresponding human molecules, the Human Leukocyte Antigene receptors, HLAs) are peptide receptors that allow the binding of millions of different ligands, with stringent specificity. The binding specifically provided by allele-specific peptide-binding motifs that have the following specificity criteria: the peptides have a defined length, which in the MHC class I haplotypes vary generally from eight to ten amino acids, while class II molecules bind peptides from a length of thirteen amino acids and above. Typically, two of the amino acid positions are so-called "anchors" which can only be occupied by a single amino acid or by amino acid groups with closely related physico-chemical properties defined by their side chains. The exact position of the anchor amino acids in the peptide and the requirements made on their properties vary with the MHC alleles. The C-terminus of the peptide ligands is frequently an aliphatic or a charged group. Examples for such peptide ligands, motifs, variants, as well as examples for extensions on the N- and/or C-terminal sides can be derived from public databases (Rammensee et al. SYFPEITHI: database for MHC ligands and peptide motifs. Immunogenetics 1999, 50, 213-219.

The protein, or fragment thereof or peptide may also be generated within the recipient mammal by introducing a nucleic acid encoding the peptide. The nucleic acid may be DNA, cDNA, PNA, CNA, RNA or a combination thereof. Methods for designing and introducing such a nucleic acid are well known in the art. An overview is provided by e.g. S. Pascolo: Vaccination with messenger RNA Methods Mol Med 2006, 127; 23-40; R. Stan, J D Wolchok and A D Cohen, DNA vaccines against cancer Hematol Oncol Clin North Am 2006, 3; 613-636 or A Mahdavi and B J Monk Recent advances in human papillomavirus vaccines Curr Oncol Rep 2006, 6, 465-472. Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun," may also be used. The peptide or peptide encoded by the nucleic acid may be a fusion protein, for example with an epitope from tetanus toxoid, which stimulates CD4+ T cells. Clinical trials using polynucleotide vaccines in cancer have been reported (e.g. Restifo and Rosenberg, Developing recombinant and synthetic vaccines for the treatment of melanoma. Curr Opin Oncol. 1999 (1): 50-57).

In a preferred embodiment aldose reductase inhibitors are administered orally while the immunotherapeutic agent is administered intradermally, subcutaneously, intravenously, intratumorally or intramuscularly. A person skilled in the art can readily determine the route of administration to choose depending of the type of composition, its solubility, dissolution, bioavailability, stability, the optional adjuvant(s) used etc.

In the method of the present invention, the aldose reductase inhibitor and at least one immunotherapy can be administered simultaneously, sequentially (sequenced over time) or separately. For example, the aldose reductase inhibitor can be administered within the same hour or within the same day as the immunotherapeutic agent, both agents may be administered on different days but within the same period of time, such as for example during the period of time of a chemotherapy regimen, or they may be administered separately.

C. Pharmaceutical Compositions and Routes of Administration

Pharmaceutical compositions of the present invention may comprise an effective amount of one or more aldose reductase inhibitors dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human. The preparation of a pharmaceutical composition can contain at least one aldose reductase inhibitor or additional active ingredient as described herein. Moreover, for animal (e.g., human) administration, it will be understood that preparations should meet sterility, pyrogenicity, general safety and purity standards as required by FDA Office of Biological Standards. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, and the like and/or combinations thereof, as would be known to one of ordinary skill in the art (see, for, example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

In addition, the aldose reductase inhibitors that may be used in accordance with this invention, prodrugs thereof and pharmaceutically acceptable salts thereof or of said prodrugs, may occur as hydrates or solvates. These hydrates and solvates are also within the scope of the invention.

A pharmaceutical composition of the present invention may comprise different types of carriers depending on whether it is to be administered in solid, liquid, or aerosol form, and whether it needs to be sterile for such routes of administration as injection. A pharmaceutical composition of the present invention can be administered intravenously, intradermally, intraarterially, intraperitoneally, intraarticularly, intrapleurally, intranasally, topically, intramuscularly, intraperitoneally, subcutaneously, subconjunctival, intravesicularlly, mucosally, intrapericardially, intraumbilically, orally, topically, locally, by inhalation (e.g., aerosol inhalation), injection, infusion, continuous infusion, via a catheter, via a lavage, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The number of doses and the period of time over which the dose may be given may vary. The practitioner responsible for administration will, in any event, determine the concentration of active ingredient(s) in a composition and appropriate dose (s), as well as the length of time for administration for the individual subject. In certain aspects an amount of an aldose reductase inhibitor that is effective for inhibiting aldose reductase activity is used. Typically, an effective dosage for the inhibitors is in the range of about 0.01 mg/kg/day to 100 mg/kg/day in single or divided doses, preferably 0.1 mg/kg/day to 20 mg/kg/day in single or divided doses. Doses of about, at least about, or at most about 0.01, 0.05, 0.1, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, to 100 mg/kg/day, or any range derivable therein. In other aspects therapeutic agents can be administered at a dose of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 500, to 700 mg, or any range derivable therein.

In certain embodiments, pharmaceutical compositions may comprise, for example, at least about 0.1% of an active compound. In other embodiments, the active compound may comprise between about 2% to about 75% of the weight of the dosage unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

An aldose reductase inhibitor(s) of the present invention may be formulated into a composition in a free base, neutral or salt form. Pharmaceutically acceptable salts include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In certain aspects of the invention, the aldose reductase inhibitors are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof, a lubricant, such as, for example, magnesium stearate; a sweetening agent, such as, for example, sucrose, lactose, saccharin or combinations thereof, a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

In particular embodiments, prolonged absorption of an injectable composition can be brought about by the use in the compositions of agents delaying absorption, such as, for example, aluminum monostearate, gelatin or combinations thereof.

In order to increase the effectiveness of treatments with the compositions of the present invention, such as an aldose reductase inhibitor, it may be desirable to combine it with other therapeutic agents (e.g., immune checkpoint inhibitors). This process may involve contacting the tissue or cell(s) with an aldose reductase inhibitor and a therapeutic agent at the same time or within a period of time wherein separate administration of the modulator and an agent to a cell, tissue, or organism produces a desired therapeutic benefit. The terms "contacted" and "exposed," when applied to a cell, tissue or organism, are used herein to describe the process by which a aldose reductase inhibitor and/or therapeutic agent (e.g., immune checkpoint inhibitor) are delivered to a target cell, tissue or organism or are placed in direct juxtaposition with the target cell, tissue or organism. The cell, tissue or organism may be contacted (e.g., by administration) with a single composition or pharmacological formulation that includes both an aldose reductase inhibitor and one or more agents, or by contacting the cell with two or more distinct compositions or formulations, wherein one composition includes an aldose reductase inhibitor and the other includes one or more agents.

The aldose reductase inhibitor may precede, be concurrent with and/or follow the other agent(s) (e.g., immune checkpoint inhibitors) by intervals ranging from minutes to weeks. In embodiments where the aldose reductase inhibitor and other agent(s) are applied separately to a cell, tissue or organism, one would generally ensure that a significant period of time did not expire between the time of each delivery, such that the inhibitor and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the modulator. In other aspects, one or more agents may be administered substantially simultaneously, or within about 1 minute, about 5 minutes, about 10 minutes, about 20 minutes about 30 minutes, about 45 minutes, about 60 minutes, about 2 hours, or more hours, or about 1 day or more days, or about 4 weeks or more weeks, or about 3 months or more months, or about one or more years, and any range derivable therein, prior to and/or after administering the aldose reductase inhibitor or therapeutic agent, respectively.

In such combinations, aldose reductase inhibitors and other active agents may be administered together or separately. In addition, the administration of one agent may be prior to, concurrent to, or subsequent to the administration of other agent(s).

In certain embodiments, the invention also provides compositions comprising 1, 2, 3 or more anti-cancer agents with one or more of the following: a pharmaceutically acceptable diluent; a carrier; a solubilizer; an emulsifier; a preservative; and/or an adjuvant. Such compositions may contain an effective amount of at least one anti-cancer agent. Thus, the use of one or more anti-cancer agents that are provided herein in the preparation of a pharmaceutical composition of a medicament is also included. Such compositions can be used in the treatment of a variety of cancer s. In certain embodiments the treatment is for melanoma or breast cancer.

The anti-cancer agents may be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular disease targeted. The compositions also preferably include pharmaceutically acceptable vehicles, carriers, or adjuvants, well known in the art.

Acceptable formulation components for pharmaceutical preparations are nontoxic to recipients at the dosages and concentrations employed. In addition to the anti-cancer agents that are provided, compositions may contain components for modifying, maintaining, or preserving, for example, the pH, osmolarity, viscosity, clarity, color, isotonicity, odor, sterility, stability, rate of dissolution or release, adsorption, or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see *Remington's Pharmaceutical Sciences*, 18 th Ed., (A. R. Gennaro, ed.), 1990, Mack Publishing Company), hereby incorporated by reference.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

In some methods of the invention, the cancer cell is a tumor cell. The cancer cell may be in a patient. The patient may have a solid tumor. In such cases, embodiments may further involve performing surgery on the patient, such as by resecting all or part of the tumor. Compositions may be administered to the patient before, after, or at the same time as surgery. In additional embodiments, patients may also be administered directly, endoscopically, intratracheally, intratumorally, intravenously, intralesionally, intramuscularly, intraperitoneally, regionally, percutaneously, topically, intrarterially, intravesically, or subcutaneously. Therapeutic compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

Methods of treating cancer may further include administering to the patient chemotherapy or radiotherapy, which may be administered more than one time. Chemotherapy includes, but is not limited to, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxotere, taxol, transplatinum, 5-fluorouracil, vincristin, vinblastin, methotrexate, gemcitabine, oxaliplatin, irinotecan, topotecan, or any analog or derivative variant thereof. Radiation therapy includes, but is not limited to, X-ray irradiation, UV-irradiation, □-irradiation, electron-beam radiation, or microwaves. Moreover, a cell or a patient may be administered a microtubule stabilizing agent, including, but not limited to, taxane, as part of methods of the invention. It is specifically contemplated that any of the compounds or derivatives or analogs, can be used with these combination therapies.

In some embodiments, the cancer that is administered the composition(s) described herein may be a bladder, blood, bone, bone marrow, brain, breast, colorectal, esophagus, gastrointestinal, head, kidney, liver, lung, nasopharynx, neck, ovary, pancreas, prostate, skin, stomach, testicular, tongue, or uterus cell. In certain aspects the cancer is colorectal cancer.

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Combination Therapy Using Aldose Reductase Inhibitors and Immune Checkpoint Inhibitors Recently, based on the promising results of pre-clinical and clinical studies on different types of cancer, targeting of the immune checkpoint proteins to prevent tumor growth has been received significant attention in the cancer immunotherapy. Hindering the interaction between the immune checkpoint proteins such as Programmed Death 1 (PD1) and Cytotoxic T-Lymphocyte-Associated protein-4 (CTLA-4) on the T-cells and PD-L1 and B7-1/B7-2 on tumor cells allows T-cells to kill tumor cells. Monoclonal antibodies against either PD-1 or PD-L1 could block the checkpoint interaction and allow T-cells to suppress the tumor growth. Clinical trials with monoclonal antibodies targeting either PD-1 or PD-L1 have shown dramatic improvement in therapeutic response and long-term regression in patients with melanoma, bladder cancer, renal carcinoma, lung cancer, Hodgkin's lymphoma, and skin cancer. Although the treatment with immune checkpoint inhibitors has brought a strong hope for cure and survival for the cancer patients, these treatments are associated with a diverse spectrum of toxicities which can be referred to as immune-related adverse events. Further, recent studies also suggest that some cancer patients become resistant to checkpoint inhibitors. Use of various combinational therapies that can improve the efficacy of immune checkpoint inhibitors as well as reduce the immune-mediated side effects is necessary to treat cancer patients successfully. The inventors have shown earlier that ARIs are anti-inflammatory as well as chemopreventive, however, the role of AR in the regulation of immune checkpoint proteins is not known. The inventors hypothesize ARIs enhance the therapeutic potential of immune checkpoint inhibitors in CRC and decrease unwanted immune-mediated adverse events.

Figure 2:
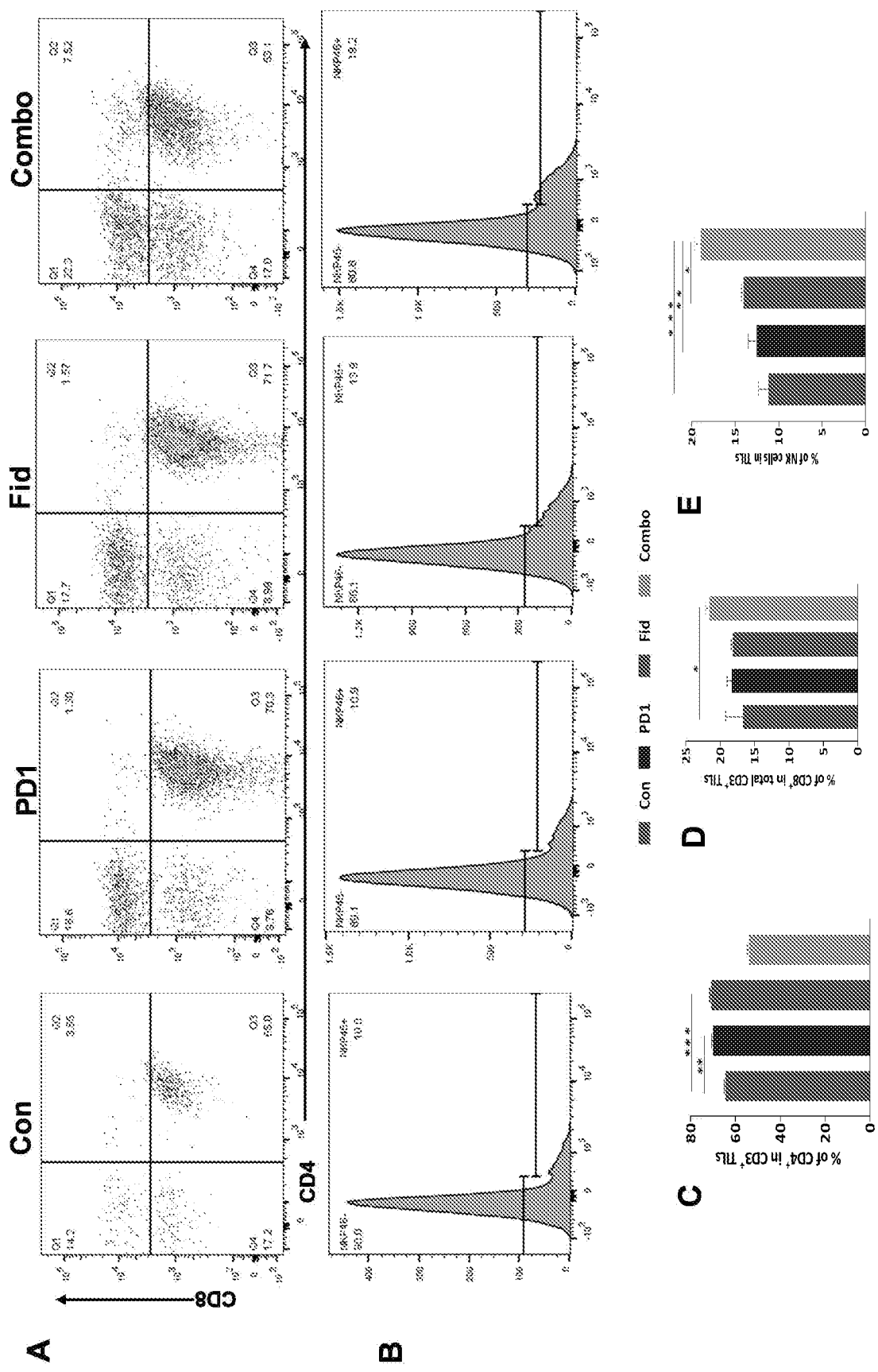
FIG. 2A-2E: Combination therapy-mediated CT26 tumor regression is dependent on $CD8^+$ T cells and NK cells. Isolated TILs from tumors were analyzed by flow cytometry for total $CD4^+$, $CD8^+$ T cells and NK cells ($NkP46^+$, B and E). Representative flow panels are shown for total $CD4^+$ and $CD8^+$ T cells (A) and NK cells (B) and pooled results from five mice are depicted in Bar graphs for $CD4^+$ (C), $CD8^+$ T cells (D) and NK cells (E). $*P<0.05$; $P<0.01$; $*P<0.001$; $****P<0.0001$ by one-way ANOVA followed by Dunnet and Tukey's multiple comparison test.
Figure 3:
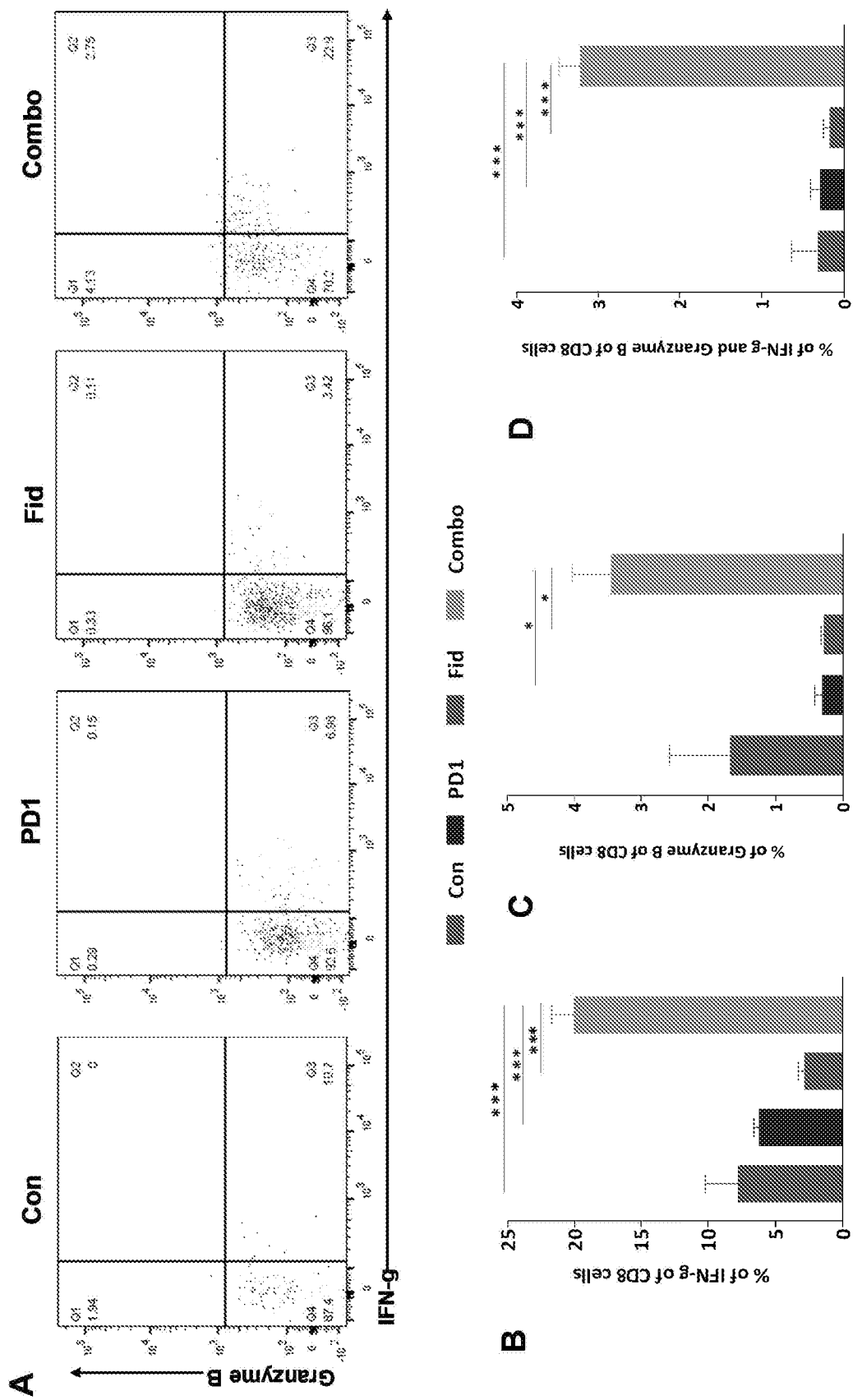
FIG. 3A-3D: Combination therapy-mediated CT-26 tumor regression is dependent on effector function of $CD8^+$ T cells. Isolated TILs from tumors were analyzed by FACS for intracellular staining of IFN-γ and granzyme B to analyze the effector function of $CD8^+$ T cells. Representative flow panels are shown for IFN-γ and granzyme B in $CD8^+$ T cells (A) and pooled results from 4-7 mice are depicted in Bar graphs for IFN-γ (B), granzyme B (C) and both (D) in $CD8^+$ T cells. $*P<0.05$; $P<0.01$; $*P<0.001$; $****P<0.0001$ by one-way ANOVA followed by Dunnet and Tukey's multiple comparison test.
Figure 4:
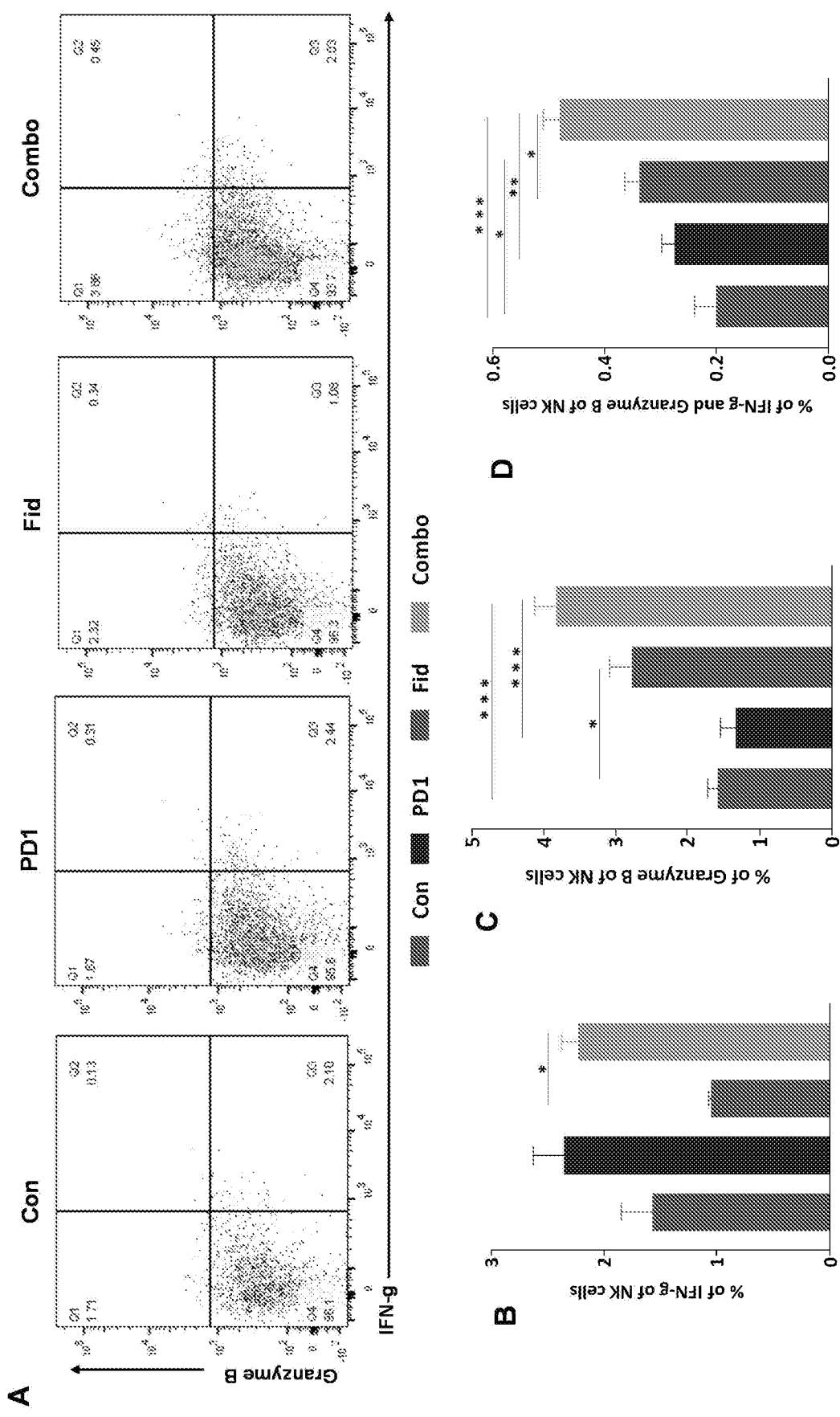
FIG. 4A-4D: Combination therapy-mediated CT26 tumor regression is dependent on effector function of NK cells. Isolated TILs from tumors were analyzed by flow cytometry for intracellular staining of IFN-γ and granzyme B to analyze the effector function of NK cells. Representative flow panels are shown for IFN-γ and granzyme B in NK cells (A) and pooled results from 4-7 mice are depicted in Bar graphs for IFN-γ (B), granzyme B (C) and both (D) in NK cells. $*P<0.05$; $P<0.01$; $*P<0.001$; $****P<0.0001$ by one-way ANOVA followed by Dunnet and Tukey's multiple comparison test.
Figure 5:
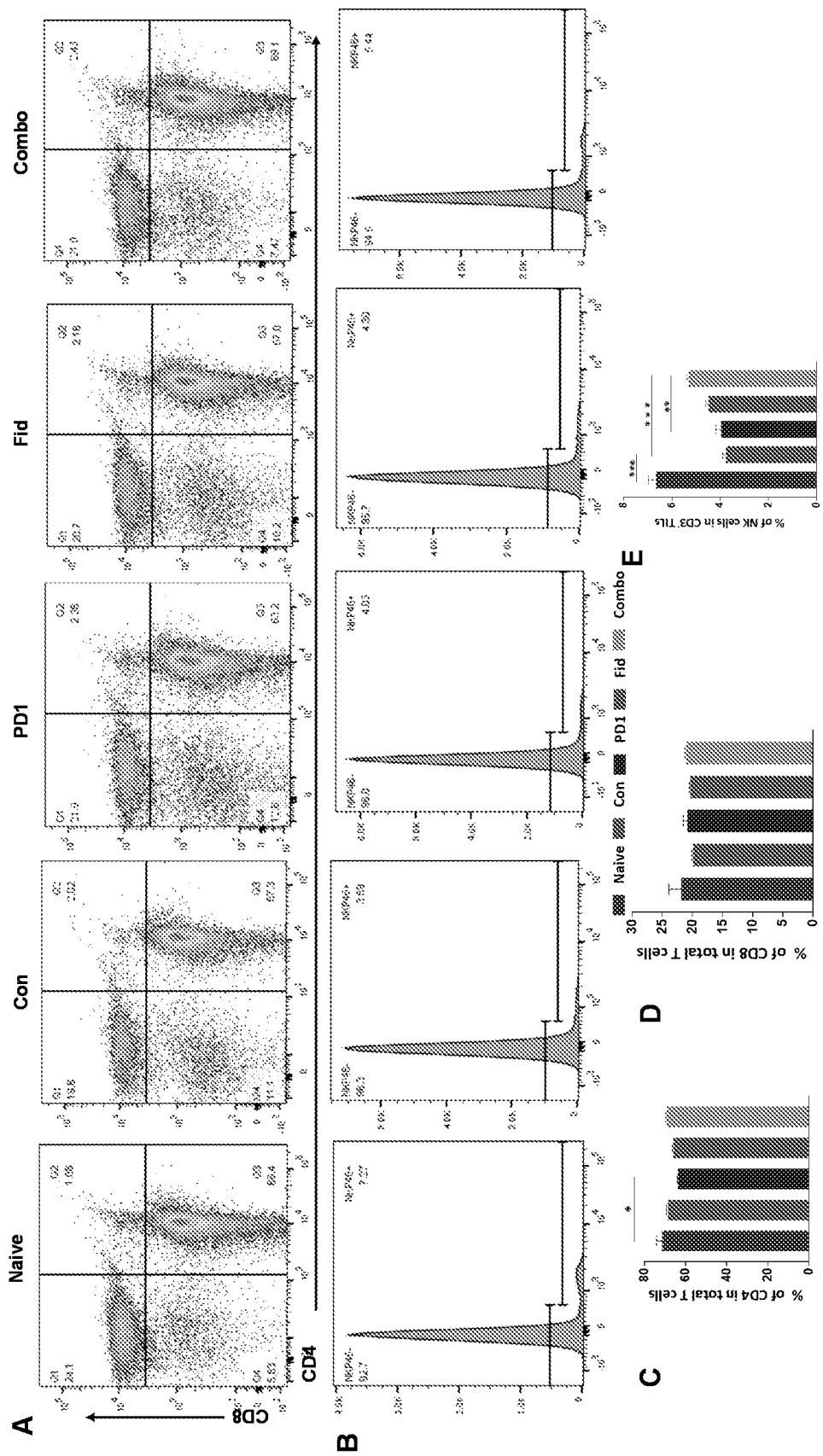
FIG. 5A-5E: Combination therapy-mediated CT26 tumor regression is dependent on $CD8^+$ T cells and NK cells. Splenocytes were analyzed by flow cytometry for total $CD4^+$, $CD8^+$ T cells and NK cells ($NkP46^+$, B and E). Representative flow panels are shown for total $CD4^+$ and $CD8^+$ T cells (A) and NK cells (B) and pooled results from 4-7 mice are depicted in Bar graphs for $CD4^+$ (C), $CD8^+$ T cells (D) and NK cells (E). $*P<0.05$; $P<0.01$; $*P<0.001$; $****P<0.0001$ by one-way ANOVA followed by Dunnet and Tukey's multiple comparison test.
Figure 6:
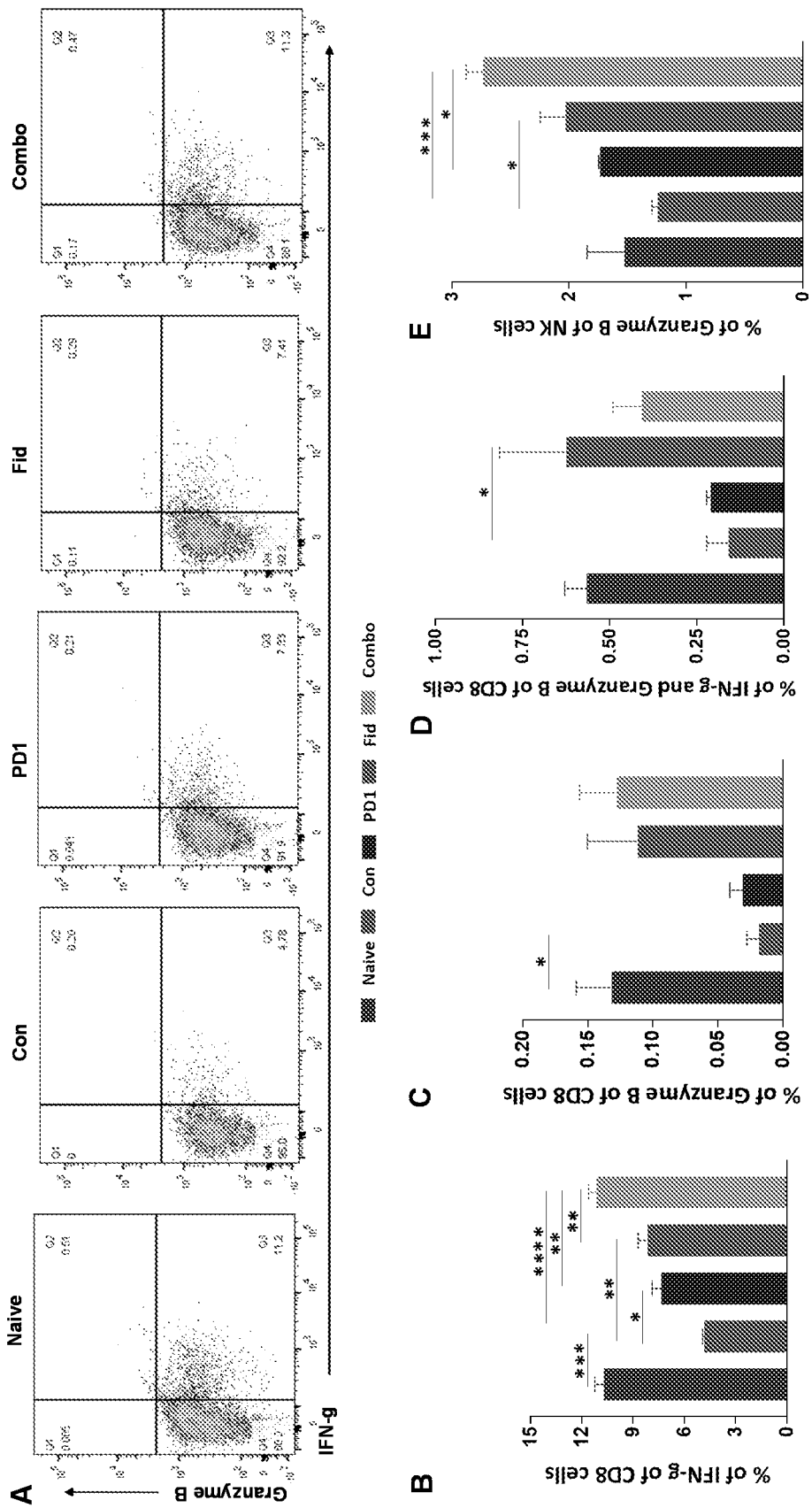
FIG. 6A-6E: Combination therapy-mediated CT26 tumor regression is dependent on effector function of $CD8^+$ T cells. Splenocytes were analyzed by flow cytometry for intracellular staining of IFN-γ and granzyme B to analyze the effector function of $CD8^+$ T cells and NK cells. Representative flow panels are shown for IFN-γ and granzyme B in CD8+ T cells (A) and pooled results from 4-7 mice are depicted in Bar graphs for IFN-γ (B), granzyme B (C) and both (D) in CD8+ T cells, and granzyme B (E) in NK cells. *P<0.05; P<0.01; *P<0.001; ****P<0.0001 by one-way ANOVA followed by Dunnet and Tukey's multiple comparison test.

The inventors' studies have demonstrated that fidarestat significantly increases the sensitivity of anti-PD1 immunotherapy. The data shown in FIG. 1 indicate that in CT-26 syngeneic Balb/c mouse model, fidarestat in combination with anti-PD1 synergistically decreases the tumor growth. Further, a combination of fidarestat with anti-PD1 significantly increased the CD8+ T-cells and NK cells among the tumor infiltrating lymphocytes isolated from tumors (FIG. 2). Fidarestat plus anti-PD1 also increased the CD8+ T-cell effector function as determined by IFNγ and granzyme B in CD8+ T-cells (FIG. 3) and NK cells (FIG. 4). Similarly, fidarestat and anti-PD1 combination increase the number of CD8+ T cells and NK cells in splenocytes isolated from syngeneic mouse (FIG. 5) and also increased their effector functions (FIG. 6). These results suggest that by increasing the CD8+ T cells and NK cells and effector functions, AR inhibitor could increase the sensitivity of anti-PD1 towards CRC therapy.

To examine how a combination of fidarestat and anti-PD1 regulates immune response in various organs, the levels of various inflammatory cytokines and chemokines in the serum, liver and heart were determined and it was found that the levels of inflammatory cytokines were significantly less in fidarestat+anti-PD1 treated mice as compared to anti-PD1 alone treated mice indicating that fidarestat rescues from immune-mediated adverse events in the organs.

Example 2

Combination Therapy Using Aldose Reductase Inhibitors and Immune Checkpoint Inhibitors in CRC Model, MC38

Figure 7:
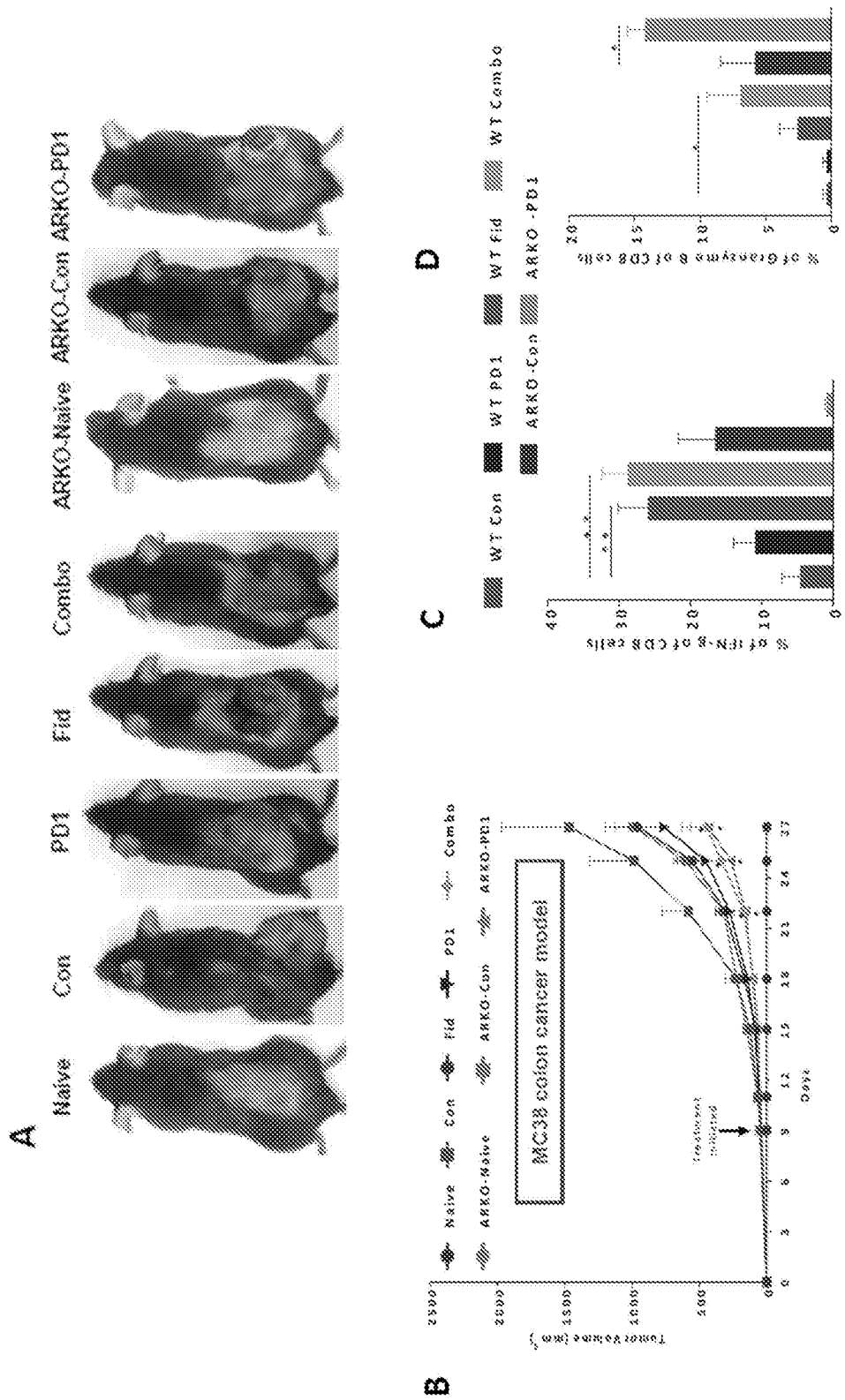
FIG. 7A-7D: AR deficiency/inhibition increases the efficacy of anti-PD1, decreases immune-related toxicities induced by anti-PD1 in CRC model, MC38. MC38 cells were inoculated subcutaneous in C57BL/6 WT and aldose reductase knockout (ARKO) mice. When tumors became palpable (approximately 40-43 mm$^3$), mice were randomized and treated with anti-PD-1 (twice a week), AR inhibitor (25 mg/kg/day in drinking water). MC38 tumor was left untreated in Con WT and ARKO or treated with Fid in WT, anti-PD-1 (PD1) in WT and ARKO or combination of both (Combo) in WT mice. Con WT and ARKO mice were also treated with isotype controls (PD-1 iso). Few mice (WT and ARKO) where the tumor was not induced served as Naïve. 6-8 mice in each group were enrolled in the study. Tumor growth was measured twice a week and animals were euthanized when the tumor volume reaches 2000 mm$^3$ in the control mice (approximately 27 days). (A) Representative image of a mouse in each group. (B) Tumor volume. Isolated TILs from tumors were analyzed by flow cytometry for intracellular staining of IFN-γ and granzyme B to analyze the effector function of CD8+ T and NK cells in TILs. Pooled results from 5-7 mice are depicted in Bar graphs for IFN-γ and granzyme B in CD8+ T cells (C, D)

Results with AR inhibitor fidarestat in CT26 model strongly suggest that AR mediates colorectal cancer progression and regulates tumor microenvironment. To examine how AR regulates immune responses and tumor growth in response to anti-PD1 therapy, how the loss-of-function of AR (AR null mice, ARKO) regulates tumor growth and efficacy of anti-PD1 in another CRC subcutaneous tumor model, MC38 was investigated in ARKO C57BL/6 mice and their WT controls. Indeed, the results demonstrated that pharmacological inhibition or deficiency of AR significantly increased the sensitivity of anti-PD1 immunotherapy. Wild type mice treated with combination therapy (WT-combo) and ARKO mice treated with anti-PD1 (ARKO-PD1) synergistically showed decreased tumor growth (FIG. 7A-7B).

MC38 cells were inoculated subcutaneous in C57BL/6 WT and aldose reductase knockout (ARKO) mice. When tumors became palpable (approximately 40-43 mm³), mice were randomized and treated with anti-PD-1 (twice a week), AR inhibitor (25 mg/kg/day in drinking water). MC38 tumor was left untreated in Con WT and ARKO or treated with Fid in WT, anti-PD-1 (PD1) in WT and ARKO or combination of both (Combo) in WT mice. Con WT and ARKO mice were also treated with isotype controls (PD-1 iso). Few mice (WT and ARKO) where the tumor was not induced served as Naïve. 6-8 mice in each group were enrolled in the study. Tumor growth was measured twice a week and animals were euthanized when the tumor volume reaches 2000 mm³ in the control mice (approximately 27 days). FIG. 7A is a representative image of a mouse in each group. FIG. 7B shows the tumor volume. Isolated TILs from tumors were analyzed by flow cytometry for intracellular staining of IFN-γ and granzyme B to analyze the effector function of CD8⁺ T and NK cells in TILs. Pooled results from 5-7 mice are depicted in Bar graphs for IFN-γ and granzyme B in CD8⁺ T cells (FIG. 7C-7D). WT-combo and ARKO-PD1 mice showed significantly increased effector functions as determined by IFN-γ and granzyme B in CD8⁺ T-cells (FIG. 7C-7D). The results show that the AR inhibitor, fidarestat increases the efficacy of anti-PD1 and decreases the tumor growth in both the CRC models.

The results with AR inhibition/deficiency in two preclinical models, CT26 and MC38 of CRC, demonstrated that by regulating the number as well as effector function of CD8⁺ T cells, NK cells and MDSCs, AR inhibitor in combination with anti-PD1 regresses the colorectal cancer tumor growth.

The invention claimed is:

1. A method of treating a subject having cancer comprising, administering (i) a composition comprising an aldose reductase specific inhibitor, wherein the aldose reductase specific inhibitor is fidarestat, and (ii) a composition comprising an immune checkpoint inhibitor, wherein the immune checkpoint inhibitor is anti-PD1, to the subject having cancer.

2. The method of claim 1, wherein the cancer is melanoma, head and neck, bladder, breast, lung, or colorectal cancer.

3. The method of claim 1, further comprising a second immune checkpoint inhibitor.

4. The method of claim 3, wherein the second immune checkpoint inhibitor and the first immune checkpoint inhibitor inhibit different pathways.

5. The method of claim 1, wherein the aldose reductase specific inhibitor is administered about 1, 2, 3, 4, 5, 6, 7, 8, 9, 10, hours or days prior to administration of the immune checkpoint inhibitor.

6. The method of claim 1, wherein the cancer is premalignant, malignant, metastatic, or drug-resistant.

7. An anti-cancer composition comprising fidarestat and anti-PD1.

* * * * *